(12) United States Patent
Hill et al.

(10) Patent No.: US 7,238,330 B2
(45) Date of Patent: Jul. 3, 2007

(54) SYSTEM AND METHOD FOR INCREASING CONCENTRATION OF STERILANT IN REGION

(75) Inventors: Aaron L. Hill, Erie, PA (US); Michael A. Bacik, Fairview, PA (US)

(73) Assignee: Steris Inc., Temecula, CA (US)

( * ) Notice: Subject to any disclaimer, the term of this patent is extended or adjusted under 35 U.S.C. 154(b) by 214 days.

(21) Appl. No.: 10/690,239

(22) Filed: Oct. 21, 2003

(65) Prior Publication Data
US 2005/0084431 A1 Apr. 21, 2005

(51) Int. Cl.
*A61L 2/00* (2006.01)
(52) U.S. Cl. .................................. 422/292; 422/305
(58) Field of Classification Search ............. 422/292, 422/305, 30
See application file for complete search history.

(56) References Cited

U.S. PATENT DOCUMENTS 5,087,419 A * 2/1992 Lutz ............................ 422/28
5,173,258 A * 12/1992 Childers .......................... 422/27
5,334,355 A * 8/1994 Faddis .......................... 422/122
5,876,664 A * 3/1999 Childers et al. .............. 422/28
5,906,794 A * 5/1999 Childers ........................ 422/28

FOREIGN PATENT DOCUMENTS

EP          1 214 103          10/2003
WO        WO 01/21223 A1 *    3/2001

* cited by examiner

*Primary Examiner*—Krisanne Jastrzab
(74) *Attorney, Agent, or Firm*—Kusner & Jaffe; Michael A. Centanni

(57) ABSTRACT

A vapor decontamination system for decontaminating a defined region. The system is comprised of a chamber defining a region, and a generator for generating vaporized hydrogen peroxide from a solution of hydrogen peroxide and water. A closed loop circulating system is provided for supplying the vaporized hydrogen peroxide to the region. A destroyer within the closed loop circulating system breaks down the vaporized hydrogen peroxide. A bypass conduit is provided to bypass the destroyer. A controller causes vaporized hydrogen peroxide from the generator to bypass the destroyer during a predetermined phase of operation.

10 Claims, 2 Drawing Sheets

SYSTEM AND METHOD FOR INCREASING CONCENTRATION OF STERILANT IN REGION

FIELD OF THE INVENTION

The present invention relates generally to the art of sterilization and decontamination, and more particularly to a system for increasing the build-up of a gaseous or vapor phase sterilant in a sterilization or decontamination system.

BACKGROUND OF THE INVENTION

Sterilization methods are used in a broad range of applications, and have used an equally broad range of sterilization agents. As used herein the term "sterilization" refers to the inactivation of all bio-contamination, especially on inanimate objects. The term "disinfectant" refers to the inactivation of organisms considered pathogenic.

Gaseous and vapor sterilization/decontamination systems rely on maintaining certain process parameters in order to achieve a target sterility or decontamination assurance level. For hydrogen peroxide vapor sterilization/decontamination systems, those parameters include the concentration of the hydrogen peroxide vapor, the degree of saturation, the temperature and pressure and the exposure time. By controlling these parameters, the desired sterility assurance levels can be successfully obtained while avoiding condensation of the hydrogen peroxide due to vapor saturation.

Conventional Vaporized Hydrogen Peroxide (VHP) sterilization systems for decontaminating large rooms or isolators are generally closed-loop systems that contain a destroyer and a dryer within the system. In such system, a sterilant is continuously conveyed through the room or isolator. Sterilant exiting the isolator or room is directed to the destroyer to break down the vaporized hydrogen peroxide into water and oxygen. This type of arrangement allows the vaporized hydrogen peroxide concentration within the system to be maintained at a desired concentration depending on the airflow and sterilant (normally 35% hydrogen peroxide, 65% water by weight in a liquid state).

During a decontamination cycle, the room or isolator to be decontaminated is first dried to a low humidity level using a desiccant dryer. After the drying phase is complete, a conditioning phase is run wherein sterilant is injected into the room or isolator at a relatively high rate to bring the hydrogen peroxide level up to a desired concentration level in a short period of time. After the conditioning phase, the decontamination phase is run where sterilant injection rate is decreased to maintain the hydrogen peroxide level at a constant concentration level. After the decontamination phase, the enclosure is aerated by turning off the sterilant injection. Aeration is run until the hydrogen peroxide level is below an allowable threshold (usually 1 ppm).

A problem with such systems, particularly during a conditioning phase, is that because the destroyer and dryer are part of the closed loop system, the vaporized hydrogen peroxide is destroyed as it exits the room or isolator to be decontaminated. As a result, the vaporizer must continuously introduce new sterilant into the air stream entering the room or isolator. This method of operation limits the rate at which the concentration of sterilant can be increased into the isolator or room during a conditioning phase. For smaller enclosures, the conditioning phase does not greatly affect the overall cycle time. However, for large rooms or isolators, i.e., areas of 5,000 ft$^3$ or larger, this can greatly affect the condition time.

The present invention overcomes this and other problems, and provides a decontamination system that increases the rate at which the concentration of a sterilant can be increased within a room or isolator.

SUMMARY OF THE INVENTION

In accordance with a preferred embodiment of the present invention, there is provided a vapor decontamination system for decontaminating a defined region. The system is comprised of a chamber defining a region, and a generator for generating vaporized hydrogen peroxide from a solution of hydrogen peroxide and water. A closed loop circulating system is provided for supplying the vaporized hydrogen peroxide to the region. A destroyer within the closed loop circulating system breaks down the vaporized hydrogen peroxide. A bypass conduit is provided to bypass the destroyer. A controller causes vaporized hydrogen peroxide from the generator to bypass the destroyer during a predetermined phase of operation.

In accordance with another aspect of the present invention, there is provided a decontamination system for decontaminating a region. The system has a generator for generating vaporized hydrogen peroxide, a closed loop system for supplying the vaporized hydrogen peroxide to the region and a destroyer for breaking down the vaporized hydrogen peroxide. A bypass conduit is provided to cause fluid flowing through the closed loop system to bypass the destroyer. A controller controls fluid flow through the bypass conduit.

In accordance with yet another aspect of the present invention, there is provided a closed loop, flow-through vapor phase decontamination system, comprising a sealable chamber that has an inlet port and an outlet port. The closed loop conduit system has a first end fluidly connected to the inlet port and a second end fluidly connected to the outlet port. A blower is connected to the conduit system for re-circulating a carrier gas flow into, through and out of the chamber. A source for delivering vaporized sterilant into the carrier gas flow is provided upstream of the inlet port. A destroyer downstream of the outlet port destroys the vaporized sterilant. A bypass conduit is provided to direct flow through the closed loop conduit system around the destroyer. A controller controls flow through the bypass conduit.

An advantage of the present invention is a system for quickly increasing the concentration of vaporized hydrogen peroxide in an enclosed chamber.

Another advantage of the present invention is a system as described above that can increase the concentration of vaporized hydrogen peroxide during a conditioning phase of a decontamination cycle.

Another advantage of the present invention is a system as described above that reduces the conditioning phase cycle time, over systems known heretofore.

A still further advantage of the present invention is a system as described above that can establish a sterilant concentration level during a conditioning phase using less sterilant.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
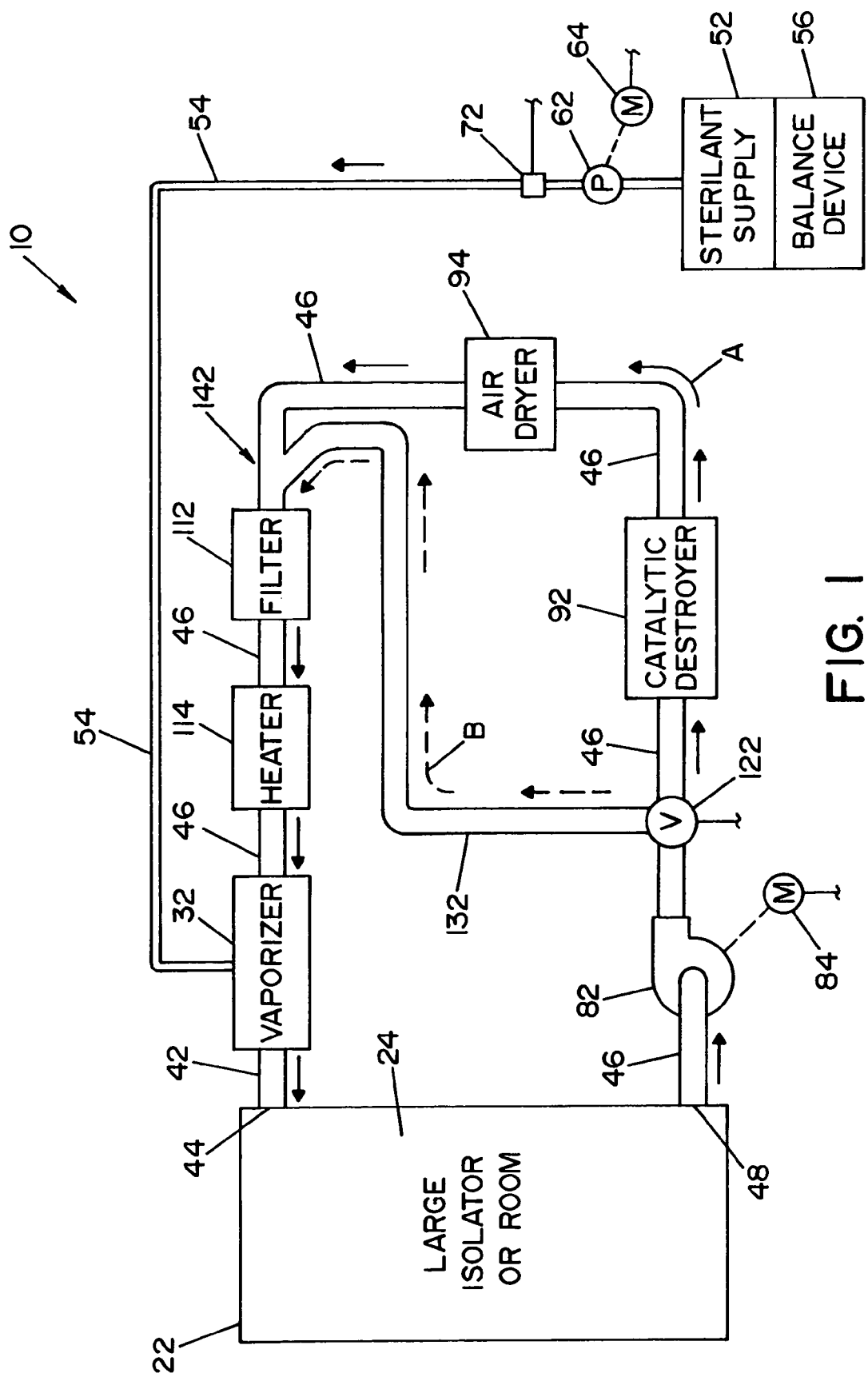
FIG. 1 is a schematic view of a vapor hydrogen peroxide deactivation system illustrating a preferred embodiment of the present invention.

Referring now to the drawings wherein the showings are for the purpose of illustrating a preferred embodiment of the invention only, and not for the purpose of limiting same, FIG. 1 shows a vaporized hydrogen peroxide sterilization system 10, illustrating a preferred embodiment of the present invention. System 10 includes an isolator or room 22 that defines an inner sterilization/decontamination chamber or region 24. It is contemplated that articles to be sterilized or decontaminated may be disposed within isolator or room 22. A vaporizer 32 (also referred to herein as generator) is connected to sterilization/decontamination chamber or region 24 of room or isolator 22 by means of a supply conduit 42. Supply conduit 42 defines a vaporized hydrogen peroxide (VHP) inlet 44 to chamber or region 24. Vaporizer 32 is connected to a liquid sterilant supply 52 by a feed line 54. A conventionally known balance device 56 is associated with sterilant supply 52, to measure the actual mass of sterilant being supplied to vaporizer 32.

A pump 62 driven by a motor 64 is provided to convey metered amounts of the liquid sterilant to vaporizer 32 where the sterilant is vaporized by conventionally known means. In an alternate embodiment, pump 62 is provided with an encoder (not shown) that allows monitoring of the amount of sterilant being metered to vaporizer 32. If an encoder is provided with pump 62, balance device 56 is not required. A pressure switch 72 is provided in the feed line. Pressure switch 72 is operable to provide an electrical signal in the event that a certain static head pressure does not exist in feed line 54.

Isolator or room 22 and vaporizer 32 are part of a closed loop system that includes a return conduit 46 that connects isolator or room 22 (and sterilization/decontamination chamber or region 24) to vaporizer 32. Return conduit 46 defines a VHP outlet 48 to sterilization/decontamination chamber or region 24. A blower 82, driven by a motor 84, is disposed within return conduit 46 between isolator or room 22 and vaporizer 32. Blower 82 is operable to circulate sterilant and air through the closed loop system. A catalytic destroyer 92 and air dryer 94 are disposed in return conduit 46 down stream from blower 82 and between blower 82 and isolator or room 22, as illustrated in FIG. 1. Catalytic destroyer 92 is operable to destroy hydrogen peroxide ($H_2O_2$) flowing therethrough, as is conventionally known. Catalytic destroyer 92 converts the hydrogen peroxide ($H_2O_2$) into water and oxygen. Air dryer 94 is operable to remove moisture from air blown through the closed loop system. A filter 112 and heater 114 are within return line 46, upstream from vaporizer 32, and between vaporizer 32 and air dryer 94. Filter 112 is operable to filter the air blown through return conduit 46 by blower 82. Heater 114 is operable to heat air blown through return conduit 46 by blower 82. In this respect, air is heated prior to the air entering vaporizer 32.

A valve 122 is disposed within return line 46 between blower 82 and catalytic destroyer 92. Valve 122 is disposed upstream of catalytic destroyer 92, as shown in FIG. 1. Valve 122 is three-way operable to control flow through return conduit 46 and a bypass conduit 132. Bypass conduit 132 is connected at one end to valve 122 and is connected at its other end to return conduit 46 at a location 142 beyond, i.e., downstream from, catalytic destroyer 92. In the embodiment shown, location 142 is also beyond, i.e., downstream from, air dryer 94.

System 10 thus defines a closed loop system having a first fluid flow path "A" and a second fluid flow path "B." First fluid flow path "A" is defined from vaporizer 32 through supply conduit 42 and chamber or region 24, and through return conduit 46, catalytic destroyer 92 and air dryer 94, as indicated by the solid arrows in FIG. 1. Second fluid flow path "B" is defined from vaporizer 32 through supply conduit 42 and chamber or region 24, and through return conduit 46 and bypass conduit 132, and back to return conduit 46 at location 142. In this respect, catalytic destroyer 92 and air dryer 94 are bypassed in second fluid flow path "B."

Figure 2:
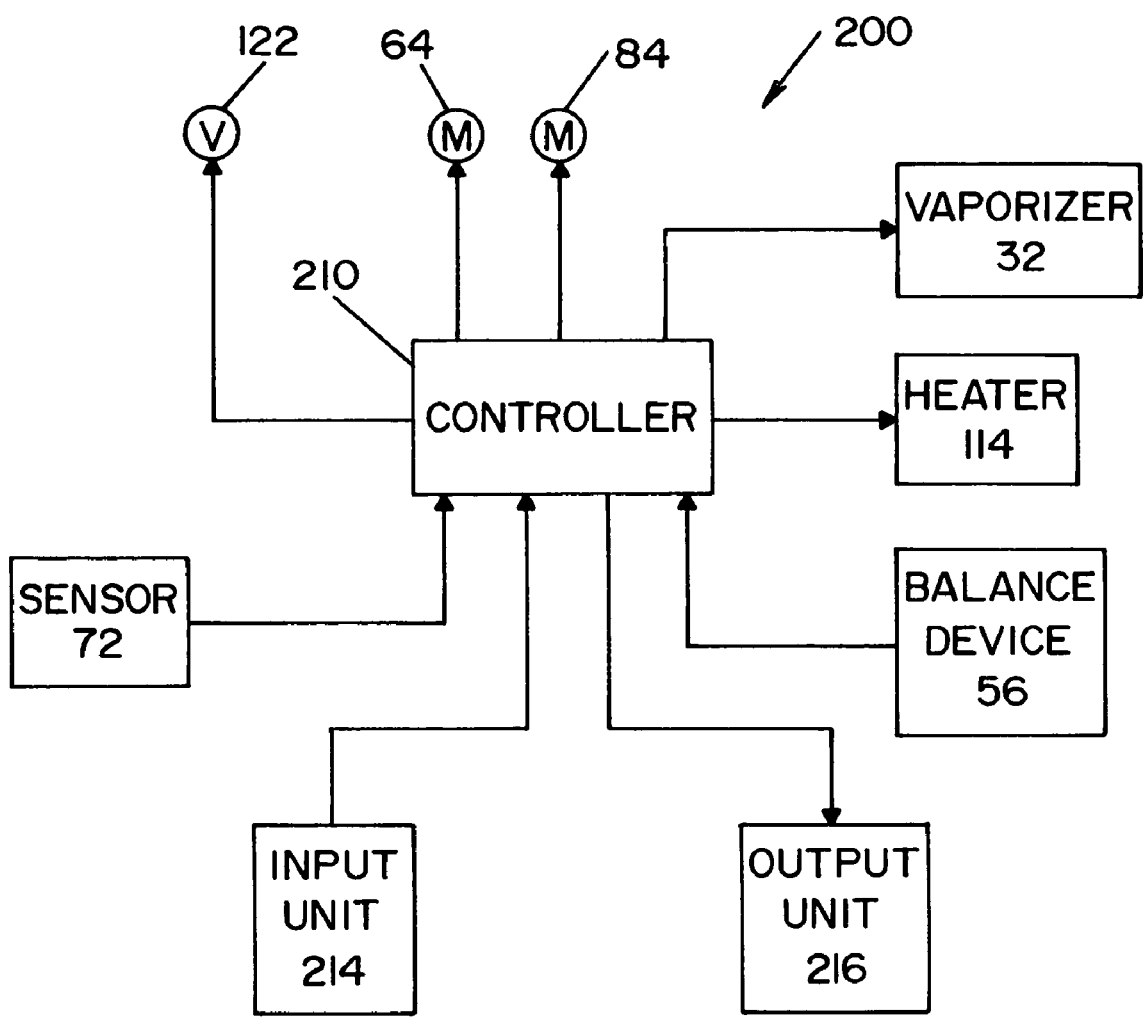
FIG. 2 is a schematic drawing of a control system for the vaporized hydrogen peroxide decontamination system shown in FIG. 1.

Referring now to FIG. 2, a control system 200 for controlling the operation of system 10 is schematically illustrated. Control system 200 includes a controller 210 that is provided to control operations of motors 64, 84 and valve 122. Controller 210 also monitors sensor 72 and balance device 56 that feeds a sterilant to vaporizer 32. Controller 210 also controls the operation of heater 114 and vaporizer 32. Controller 210 is a system microprocessor or a microcontroller that is programmed to control the operation of system 10.

An input unit 214 is provided and attached to controller 210 to allow a user of system 10 to input operation parameters. Input unit 214 may be any device that would facilitate the input of data and information to controller 210 by a user of system 10, such as by way of example and not limitation, a keypad, a keyboard, a touch screen or switches. An output unit 216 is also connected to controller 210. Output unit 216 is provided to enable controller 210 to provide information to the user on the operation of system 10. Output unit 216 may be, by way of example and not limitation, a printer, display screen or LED display. Controller 210 is programmed such that system 10 operates in certain operating phases.

The present invention shall now be further described with reference to the operation of system 10. A typical sterilization/decontamination cycle includes a drying phase, a conditioning phase, a decontamination phase and an aeration phase. Prior to running a sterilization/decontamination cycle, data regarding the percent of hydrogen peroxide in the sterilant solution is entered, i.e., inputted, into controller 210. As noted above, in a preferred embodiment a sterilant solution of 35% hydrogen peroxide by weight and 65% water by weight is used. However, other concentrations of hydrogen peroxide and water are contemplated.

When a sterilization/decontamination cycle is first initiated, controller 210 causes blower motor 84 to drive blower 82, thereby causing a carrier gas to circulate through system 10. During a drying phase, vaporizer 32 is not operating. Valve 122 is in a position allowing fluid to flow along first fluid flow path "A." Air dryer 94 removes moisture from the air circulating through first fluid flow path "A," i.e., through supply conduit 42, sterilization/decontamination chamber or region 24 of isolator or room 22, return conduit 46 and catalytic destroyer 92 and air dryer 94. When the air has been dried to a sufficiently low humidity level, the drying phase is complete.

The conditioning phase is then initiated. Controller 210 causes valve 122 to move to a position allowing fluid flow only along second fluid path "B," thereby bypassing catalytic destroyer 92 and air dryer 94. Controller 210 activates vaporizer 32 and sterilant supply motor 64 to provide sterilant to vaporizer 32. In a preferred embodiment of the present invention, the sterilant is a hydrogen peroxide solution comprised of about 35% by weight hydrogen peroxide and about 65% by weight water. A sterilant solution comprised of different ratios of hydrogen peroxide is also contemplated. Within vaporizer 32, the liquid sterilant is vaporized to produce vaporized hydrogen peroxide (VHP) and water vapor, in a conventionally known manner. The vaporized sterilant is introduced into the closed loop conduit circuit and is conveyed through supply conduit 42 by the carrier gas (air) into sterilization/decontamination chamber or region 24 within isolator or room 22. During the conditioning phase, vaporized hydrogen peroxide is injected into sterilization/decontamination chamber or region 24 at a relatively high rate to bring the hydrogen peroxide level up to a desired level in a short period of time. During the conditioning phase, blower 82 causes air to continuously circulate through second fluid flow path "B" as vaporized hydrogen peroxide enters chamber or region 24 from vaporizer 32. Vaporized hydrogen peroxide exiting chamber or region 24 is directed through bypass conduit 132, thereby bypassing catalytic destroyer 92.

As a result of the continuous circulation of the vaporized hydrogen peroxide (VHP) along second fluid flow path B, the concentration of vaporized hydrogen peroxide (VHP) in chamber or region 24 increases more rapidly than would be the case if the vaporized hydrogen peroxide (VHP) were destroyed by catalytic destroyer 92 as the vaporized hydrogen peroxide (VHP) exited chamber or region 24. The vaporized hydrogen peroxide (VHP) continuously circulates through system 10 and back through vaporizer 32 where additional vaporized hydrogen peroxide (VHP) is generated and added to the flow of vaporized hydrogen peroxide (VHP).

After the conditioning phase is completed, the decontamination phase is initiated. During the decontamination phase, the sterilant injection rate to vaporizer 32 and to sterilization/decontamination chamber or region 24 is decreased to maintain the concentration of vaporized hydrogen peroxide (VHP) constant and at a desired level. Controller 210 causes valve 122 to move to a position directing fluid flow in system 10 through first fluid flow path A, wherein the flow is directed through catalytic destroyer 92 and air dryer 94. Catalytic destroyer 92 breaks down the vaporized hydrogen peroxide flowing therethrough into water and oxygen. Thus, the concentration of vaporized hydrogen peroxide (VHP) within chamber or region 24 is determined by the output of vaporizer 32. The decontamination phase is run for a predetermined period of time, preferably with the vaporized hydrogen peroxide (VHP) concentration remaining constant at a desired level, for a predetermined period of time that is sufficient to effect the desired sterilization or decontamination of sterilization/decontamination chamber or region 24, and/or items therein.

After the decontamination phase is completed, controller 210 causes vaporizer 32 to shut down, thereby shutting off the flow of vaporized hydrogen peroxide (VHP) into sterilization/decontamination chamber or region 24.

Thereafter, the aeration phase is run to bring the vaporized hydrogen peroxide (VHP) level down to an allowable threshold (about 1 ppm). In this respect, as will be appreciated, blower 82 continues to circulate the air and sterilant through the closed loop system, thereby causing the last of the vaporized hydrogen peroxide (VHP) to be broken down by catalytic destroyer 92.

The present invention thus provides a simple yet efficient method of increasing the amount of vaporized hydrogen peroxide (VHP) within sterilization/decontamination chamber or region 24 during a conditioning phase. The present invention is preferably used with large chambers or regions 24, such as enclosures of 3,000 $ft^3$ or larger, and preferably enclosures of 5,000 $ft^3$ or larger.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A vapor decontamination system for decontaminating a defined region, said system comprising:
    a chamber defining a region;
    a closed loop circulating system for supplying said vaporized hydrogen peroxide to said region, said closed loop circulating system defining a first fluid path;
    a generator disposed within said first fluid path, said generator being operable to generate vaporized hydrogen peroxide from a solution of hydrogen peroxide and water;
    a destroyer for breaking down said vaporized hydrogen peroxide disposed within said first fluid path upstream of said generator;
    a bypass conduit bypassing a portion of said first fluid flow path, said destroyer being disposed in said portion of said first fluid flow path, said bypass conduit having a first end fluidly connected to said first fluid path between said region and said destroyer and a second end fluidly connected to said first flow path between said destroyer and said generator;
    a valve disposed at said first end of said bypass conduit, said valve having a first position for directing fluid flowing along said first fluid flow path though said portion of said first fluid flow path, and a second position for directing fluid flowing along said first fluid flow path though said bypass conduit bypassing said portion of said first fluid flow path and said destroyer; and
    a controller operable to cause substantially all of said vaporized hydrogen peroxide generated by said generator to bypass said destroyer during a predetermined phase of operation.

2. A vapor decontamination system as defined in claim 1, wherein said controller is programmed to include a drying phase of operation, a conditioning phase of operation, a decontamination phase of operation and an aeration phase of operation.

3. A vapor decontamination system as defined in claim 2, wherein said controller causes substantially all of said vaporized hydrogen peroxide to bypass said destroyer during said conditioning phase.

4. A vapor decontamination system as defined in claim 1, further comprising an air dryer downstream from said destroyer.

5. A vapor decontamination system as defined in claim 4, wherein said air dryer is disposed within said portion of said first fluid flow path.

6. A closed loop, flow-through vapor phase decontamination system, comprising:
- a sealable chamber having an inlet port and an outlet port;
- a closed loop conduit system having a first end fluidly connected to said inlet port and a second end fluidly connected to said outlet port, said closed loop conduit system defining a first fluid path for circulating a vapor phase decontaminant through said sealable chamber;
- a blower for re-circulating a carrier gas flow into, through and out of the chamber;
- a source for delivering vaporized sterilant into said carrier gas flow upstream of said inlet port;
- a destroyer downstream of said outlet port for destroying the vaporized sterilant, wherein said blower, said source for delivering vaporized sterilant, and said destroyer are disposed within a first fluid path;
- a bypass conduit connected to said closed loop conduit system, said bypass conduit defining a second fluid path that bypasses a portion of said first fluid path, said destroyer being disposed in said portion of said first fluid path that is bypassed by said bypass conduit, and said blower and said source for delivering said vaporized sterilant being disposed within said second fluid path;
- a valve associated with said bypass conduit, said valve having a first position for directing said carrier gas along said first fluid path and a second position directing said carrier gas along said second fluid path; and
- a controller for controlling the position of said valve.

7. A system as defined in claim 6, wherein said sterilant is vaporized hydrogen peroxide.

8. A system as defined in claim 7, wherein said controller directs flow only through said second fluid flow path during a conditioning phase of operation.

9. A system as defined in claim 6, further comprising an air dryer disposed downstream from said destroyer.

10. A system as defined in claim 9, wherein said blower is disposed downstream from said chamber, between said destroyer and said chamber.

* * * * *